United States Patent
Grard

[11] 3,983,177
[45] Sept. 28, 1976

[54] PROCESS FOR THE PREPARATION OF UNSATURATED KETONES

[75] Inventor: Charles Grard, Chaponost, France

[73] Assignee: Rhone-Poulenc S.A., Paris, France

[22] Filed: June 23, 1972

[21] Appl. No.: 265,601

[30] Foreign Application Priority Data
June 24, 1971 France .............................. 71.23063

[52] U.S. Cl. .................... 260/593 R; 260/586 C; 260/586 R; 260/590 E; 260/591; 260/598; 260/599; 260/601 R
[51] Int. Cl.² ........................................ C07C 49/20
[58] Field of Search ........ 260/593 R, 586 C, 586 R, 260/590 E, 591

[56] References Cited
OTHER PUBLICATIONS
Savcy et al., "Heliutica Chemica Acta," vol. 50, pp. 2091-2095, (1967).

Primary Examiner—Nicholas S. Rizzo
Assistant Examiner—D. B. Springer
Attorney, Agent, or Firm—Cushman, Darby & Cushman

[57] ABSTRACT
Ketones, which are intermediates in the synthesis of vitamin A or perfumes, and have the general formula:

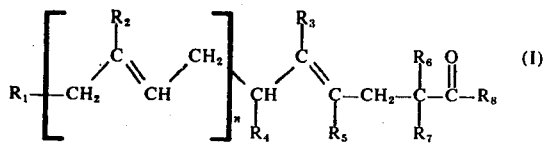

wherein $R_1$ is hydrogen or $C_{1-10}$ hydrocarbon, $R_2$ and $R_3$ are hydrogen or $C_{1-4}$ alkyl, $R_4$ and $R_5$ are hydrogen or together form a $-CH_2-CH_2-C(CH_3)_2-$ group, $R_6$ and $R_7$ are hydrogen or $C_{1-10}$ hydrocarbon, or together with the carbon atom to which they are joined form a hydrocarbon ring of up to 10 carbons, or

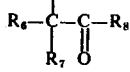

forms a hydrocarbon ring of up to 10 carbons joined through $R_6$ and $R_8$ or $R_7$ and $R_8$, $R_8$ is hydrogen or $C_{1-10}$ hydrocarbon and $n$ is 0–6, are prepared by reacting an unsaturated halide of formula

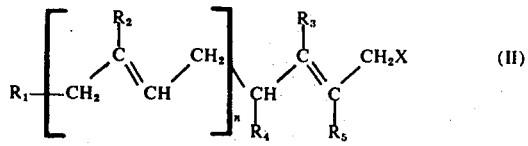

wherein X is halogen, with an enol ester of formula

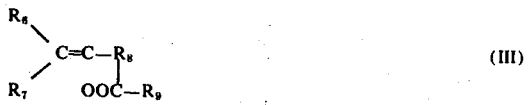

wherein $R_9$ is $C_{1-20}$ hydrocarbon, in the presence of a metal catalyst.

14 Claims, No Drawings

PROCESS FOR THE PREPARATION OF UNSATURATED KETONES

The present invention relates to a process for preparing unsaturated ketones and to the ketones produced.

The present invention provides a process for the preparation of a ketone of the general formula:

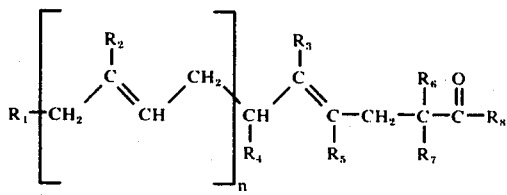

in which:

$R_1$ represents a hydrogen atom or a saturated or unsaturated linear, branched or cyclic, hydrocarbon group containing up to 10 carbon atoms, such as an alkyl group (e.g. methyl, ethyl, propyl and octyl), and alkenyl or alkadienyl group (e.g. 3,7-dimethyl-hexa-2,6-dienyl), a cycloalkyl group (e.g. cyclohexyl and 6,6-dimethyl-cyclohexyl), a cycloalkenylgroup (e.g. cyclohexenyl, 6,6-dimethyl-cyclohex-1-enyl, 2,6,6-trimethyl-cyclohex-1-enyl and 2,6,6-trimethyl-cyclohex-2-enyl) or an aryl group (e.g. phenyl), each of $R_2$ and $R_3$, which may be the same or different, represents a hydrogen atom or an alkyl group of 1 to 4 carbon atoms preferably a methyl group, $R_4$ and $R_5$ represent hydrogen atoms or, together they form a divalent hydrocarbon group of the formula

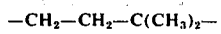

each of $R_6$ and $R_7$, which may be the same or different, represents a hydrogen atom or a saturated or unsaturated, linear, branched or cyclic, hydrocarbon group containing up to 10 carbon atoms, or $R_6$ and $R_7$ together with the carbon atom, to which they are attached, form a hydrocarbon ring of up to 10 carbon atoms, or the group

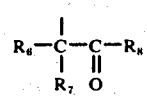

forms a hydrocarbon ring of up to 10 carbon atoms joined through $R_6$ and $R_8$, or $R_7$ and $R_8$. $R_8$ represent a saturated or unsaturated, linear, branched or cyclic hydrocarbon group containing up to 10 carbon atoms, and $n$ is 0 or an integer of 1 to 6, wherein an unsaturated halide of the general formula:

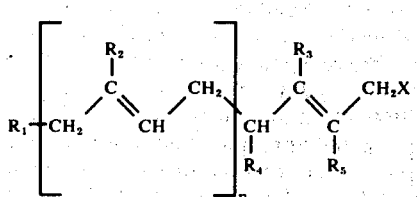

in which X represents a halogen atom and each of $R_1$, $R_2$, $R_3$, $R_4$ and $R_5$ is as defined above, is reacted with an ester of the enol form of a ketone, the ester being of the general formula:

in which each of $R_6$, $R_7$ and $R_8$ is as defined above and $R_9$ represents a saturated or unsaturated, linear, branched or cyclic, hydrocarbon group containing up to 20 carbon atoms, in the presence of a catalyst which is at least one metal (or derivative thereof) from groups 1b, 2b, 3b, 4a, 4b, 5a, 5b, 6b, 7b and 8 of the periodic classification (including the actinide group).

The process of the invention is preferably used for preparing products of the formula (I) in which $R_1$ has the specific meanings given above, $R_2$, $R_3$, $R_4$ and $R_5$ are as defined above and $R_6$, $R_7$, $R_8$ and $R_9$ have the following meanings: each of $R_6$ and $R_7$ represents an alkyl group (e.g. methyl, ethyl, propyl, butyl and octyl), a cycloalkyl group (e.g. cyclohexyl) or an aryl group (e.g. phenyl); $R_8$ represents an alkyl group (e.g. methyl, ethyl, propyl, isopropyl, butyl and octyl), a cycloalkyl group (e.g. cyclohexyl), an aryl group (e.g. phenyl), an aralkyl group (e.g. benzyl) or an alkylaryl group (e.g. toluyl); $R_9$ represents an alkyl group (e.g. methyl, ethyl, propyl, butyl and decyl), an alkenyl group (e.g. undecenyl and pentadecenyl), a cycloalkyl group (e.g. cyclohexyl) or an aryl group (e.g. phenyl and naphthyl).

Examples of halides of the formula (II), are:
1-chloro-3-methyl-2-butene
1-bromo-3-methyl-2-butene
geranyl chloride
geranyl bromide
farnesyl chloride
farnesyl bromide
1-chloromethyl-2,6,6-trimethyl-cyclohexene
6-chloromethyl-1,5,5,-trimethyl-cyclohexene and
1-[5-chloro-3-methyl-pent-3-enyl]-2,6,6-trimethyl-cyclohexene.

Examples of enol esters of the formula (III), are:
2-propenyl acetate
2-propenyl benzoate
but-1-en -2-yl acetate
but-2-en -3-yl acetate
4-methyl-pent-1-en -2-yl acetate
4-methyl-pent-2-en -3-yl propionate
buta-1,3-dien -2-yl acetate
penta-1,3-dien -2-yl acetate
penta-2,4-dien -2-yl acetate
3-methyl-buta-1,3-dien -2-yl acetate
2-cyclohexenyl acetate and
α-acetoxy-styrene.

The condensation of the unsaturated halides of the formula (II) with the enol esters of the formula (III) can be represented by the following equation:

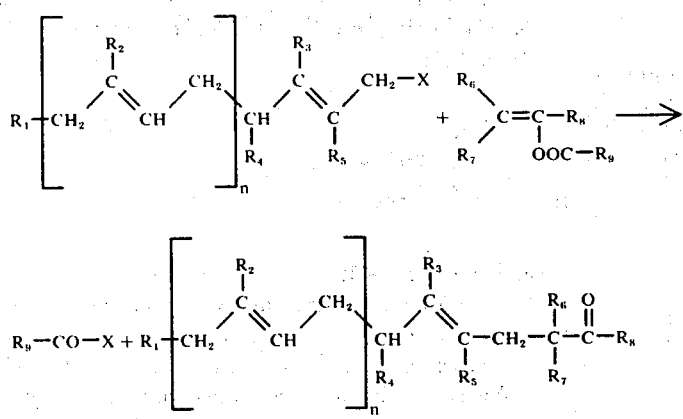

During the reaction, an acid halide, an important industrial product is formed and can be separated easily from the other compounds present in the reaction medium by the usual methods.

The metal used as the catalyst in the process of the invention is chosen from the groups 1b, 2b, 3b, 4b, 5b, 6b, 7b, 4a, 5a and 8 of the periodic classification of the elements given in Handbook of Chemistry and Physics, 45th Edition, p. B-2 (including the actinide group). The following metals are preferred: U, Zr, Mo, W, Mn, Fe, Ru, Os, Co, Cu, Ni, Zn, Cd, Sn, Pb, Sb, Re and Au.

The catalyst can be used in the form of free metal or in the form of a derivative, the nature of the radical combined with the metal in the derivative being not critical. For example, it can be an anion of an inorganic or organic acid, such as a halide (e.g. chloride or bromide), sulphate, phosphate, nitrate, acetate, benzoate, octoate, naphthenate or stearate anion. It can also be a monodentate or polydentate ligand (e.g. carbonyl or β-diketone). Examples of metal derivatives are ferrous chloride, ferric chloride, ruthenium chloride, cobalt chloride, stannous hydroxide, stannous and stannic chlorides, zinc acetate, stannous acetate, stannic acetate, ferrous acetate, uranyl acetate, cobalt octoate, cobalt naphthenate, ferric acetyl acetonate and iron pentacarbonyl.

The amount of catalyst, expressed as the number of gram atoms of metal or gram ions of metal ion per mole of unsaturated halide (II), can vary within wide limits. Generally, an amount of catalyst corresponding to an amount of metal of between $1 \times 10^{-5}$ (and especially 0.0001) and 0.2 gram atom of metal or gram ion of metal ion per mole of unsaturated halide (II) is quite suitable. An amount of catalyst corresponding to more than 0.2 gram atoms of metal per mole of halide can be used, but this is of no particular value.

The temperature at which the reaction is carried out depends on the reagents employed. Generally, a temperature of between −50°C and +200°C, and preferably between −20°C and +150°C, is satisfactory. The reaction can be carried out at normal pressure or at a pressure which is greater or less than 1 bar. A simple experiment allows the most favourable temperature to be chosen in each case.

The condensation of the unsaturated halide with the enol ester can be carried out, equally well in the presence or absence of an inert organic solvent. The solvent is preferably an aliphatic or cycloaliphatic hydrocarbon (e.g. hexane or cyclohexane), an ether (e.g. diethyl ether, tetrahydrofuran or diglyme) a halogenated derivative (e.g. chloroform or carbon tetrachloride) or a ketone (e.g. acetone). If a ketone is used as the diluent, the ketone corresponding to the enol ester employed in the process is preferably used.

Although the reaction involves one mole of halide of formula (II) with one mole of enol ester, of formula (III), it is preferable to carry out the reaction with an excess of enol ester representing at least 0.5 mole per mole of halide. If the enol ester is a liquid under the conditions of the reaction it can be used as the reaction medium since there is no critical upper limit to the excess of enol ester which can be employed.

The process of the invention is suitable for the preparation of linear ketones, especially those containing reduced isoprene linkages, used as intermediates in the synthesis of perfumes or of vitamin A. In particular, the process claimed is very valuable for the preparation of 2-methylhept-2-en-6-one.

The invention is illustrated in the following Examples:

EXAMPLE 1

Isopropenyl acetate (500 g, 5 mole) and stannous acetate (0.296 g, $1.25 \times 10^{-2}$ g.ion $Sn^{2+}$) are introduced into a 1 liter flask equipped with a stirring system, a dropping funnel and a reflux condenser, and heated on an oil bath.

The contents of the flask are heated to the reflux temperature, and then 26.1 g (0.25 mole) of 1-chloro-3-methyl-2-butene are added, over a period of 40 minutes. The reaction mixture gradually turns red. Heating under reflux is continued for a further hour after the end of the addition of the chlorinated derivative, and then the heating is stopped and the reaction mixture is cooled to 0°C. On distillation under a water pump vacuum, 482 g of a product are removed containing 460.5 g of isopropenyl acetate 4.15 g of 1-chloro-3-methyl-2-butene and 15.1 g of acetyl chloride.

The residue obtained is treated with 100 cm³ of a normula aqueous solution of sodium hydroxide, washed until neutral, dried over $Na_2SO_4$ and distilled under a pressure reduced to 18 mm of mercury. In this way, 12 g of isopropenyl acetate and 18 g of a fraction, containing 96% (17.3 g) of methylheptenone (as determined by gas-liquid chromatography) are recovered.

The degree of conversion of 1-chloro-3methyl-2-butene is 84.5% and the yield of methylheptenone is 65% relative to the converted chloride.

The fraction containing the methylheptenone is rectified, allowing a 99% pure product to be obtained, the IR, NMR and mass spectra of which are identical to those of a sample pure product.

The above experiment was repeated in the absence of a tin salt. After 8 hours of heating under reflux, it was not possible to detect any methylheptenone in the contents of the flask.

EXAMPLE 2

The procedure of Example 1 is repeated with the isopropenyl acetate replaced by isopropenyl benzoate added over a period of 7 minutes and the reaction mixture is maintained under reflux for 1 hour 20 minutes after the introduction of the reagents. In this experiment, isopropenyl benzoate (24.3g.0.15 mole) 1-chloro-3methyl-2-butene (3.15 g., 0.03 mole) and stannous acetate (0.0345 g., $1.5 \times 10^{-5}$g. ion $Sn^{++}$) are introduced.

At the end of the reaction, 0.8 g of methylheptenone and 2.4 g of benzoyl chloride are recovered. The degree of conversion of 1-chloro-3methyl-2-butene is 95%.

EXAMPLE 3

The procedure of Example 1 is repeated, using isopropenyl acetate (200 g, 2 moles), 1-chloro-3-methyl-2-butene (10.45 g, 0.1 mole) and molybdenum (II) acetate (0.214 g, 0.001 g.ion $Mo^{++}$).

At the end of the reaction, 1.8 g of 1-chloro-3-methyl-2-butene are recovered and 4.2 g. of methylheptenone are found. The degree of conversion is 83% and the yield of methylheptenone relative to the converted chloride is 37%.

EXAMPLE 4

The procedure of Example 1 is repeated, using isopropenyl acetate (75 g, 0.75 mole) 1-chloro-3-methyl-2-butene (10.45 g, 0.1 mole) $RuCl_3$-$\alpha$ (0.108 g, $5 \times 10^{-4}$g.ion $Ru^{++}$).

At the end of the reaction, 0.7 g of chloride (degree of conversion 93%) is recovered and 4.24 g of methylheptenone (yield: 36% relative to the converted chloride) are found.

EXAMPLE 5

The procedure of the preceding Examples is repeated, using isopropenyl acetate (200 g, 2 moles), 1-chloro-3-methyl-2-butene (10.45 g, 0.1 mole), and zinc acetate (0.224 g. 0.001 g. ion $Zn^{++}$)

The degree of conversion of the chloride is 100% and the amount of methylheptenone found is 3.6 g (yield/converted chloride: 28%).

EXAMPLE 6

The procedure of the preceding Example is repeated, using isopropenyl acetate (35 g, 0.35 mole), 1-chloro-3-methyl-2-butene (10.45 g, 0.1 mole) and $FeCl_3$ (0.1 g, $6.2 \times 10^{-4}$g.ion $Fe^{+++}$).

At the end of the reaction, 6 g of chloride (degree of conversion 36.6%) are recovered and 2 g of methylheptenone (yield/converted chloride: 40%) are found.

EXAMPLE 7

The procedure of the preceding Examples is repeated, using isopropenyl acetate (200 g, 2 moles), 1-chloro-3-methyl-2-butene (10.45 g, 0.1 mole) uranyl acetate (0.424 g, $10^{-3}$ g ion $U^{6+}$).

At the end of the reaction, 0.45 g of chloride (degree of conversion 96.2%) is recovered and 4.85 g of methylheptenone (yield/converted chloride: 40%) are found.

EXAMPLE 8

120 g of diglyme and 0.08 g of $FeCl_3$ (0.0005 g.ion $Fe^{3+}$) are introduced into the apparatus described in Example 1. The contents of the flask are heated to 100°C, and then a mixture of 20 g of isopropenyl acetate and 5.2 g of 1-chloro-3-methyl-2-butene is added over a period of 45 minutes. The heating of the assembly is continued for 2 hours. The reaction mixture is then steam distilled, the organic layer (4 g) is isolated and then rectified to yield 1.5 g of methylheptenone.

EXAMPLE 9

40 g of isopropenyl acetate (0.4 mole), 10.45 g of 1-chloro-3-methyl-2-butene (0.1 mole) and 0.09 g of $FeCl_3$ ($5.7 \times 10^{-4}$ g. ion $Fe^{3+}$) are introduced into an apparatus identical to that used in Example 1. The flask is cooled to −20°C and then the temperature is allowed to increase slowly to 20°C again. 1.7 g of methylheptenone are recovered. The degree of conversion of the chloride is 75% and the yield/converted chloride is 18%.

EXAMPLE 10

20 g of isopropenyl acetate (0.2 mole), 5.2 g of 1-chloro-3-methyl-2-butene (0.05 mole) and 0.354 g of ferric acetylacetonate ($10^{-3}$g.ion $Fe^{3+}$) are introduced into ann apparatus identical to that used in Example 1. The contents of the flask are heated under reflux for 2 hours. 0.76 g of unconverted chloride (degree of conversion 85%) and 1.15 g of methylheptenone (yield/converted chloride: 21%) are recovered.

EXAMPLE 11

The procedure of Example 1 is employed using isopropenyl acetate (100 g, 1 mole), 1-chloro-3-methyl-2-butene (10.45 g, 0.1 mole) and $ReCl_3$ (0.146 g, $5 \times 10^{-4}$ g.ion $Re^{3+}$).

At the end of the reaction, 7.15 g of chloride (extent of conversion 31.5%) and 1.27 g of methylheptenone (yield/converted chloride: 32.5% are recovered.

EXAMPLES 12 to 15

Employing the procedure of Example 1, a series of experiments with various catalysts was carried out. The results are shown in Table 1.

TABLE 1

| EX. | REAGENTS INTRODUCED | | CATALYST | | DURATION OF REFLUX | EXTENT OF CONVERSION of CMB, % | YIELD MH(3)/ CONVERTED CMB |
|---|---|---|---|---|---|---|---|
| | I.A.(1) | CMB(2) | NATURE | WEIGHT | | | |
| 12 | 200 g | 10.45 g | $Sn(OH)_2$ | 0.076 g | 1 hr 40 min | 88 | 42 |
| 13 | 200 g | 10.45 g | Fe powder | 0.028 g | 1 hr | 66 | 48 |
| 14 | 20 g | 10.45 g | $ZrCl_4$ | 0.116 g | 1 hr | 86 | 9.6 |

TABLE 1-continued

| EX. | REAGENTS INTRODUCED | | CATALYST | | DURATION OF REFLUX | EXTENT OF CONVERSION of CMB, % | YIELD MH(3)/ CONVERTED CMB |
|---|---|---|---|---|---|---|---|
| | I.A.(1) | CMB(2) | NATURE | WEIGHT | | | |
| 15 | 200 g | 10.45 g | SnCl$_2$ | 0.095 g | 1 hr 28 min | 63.5 | 50 |

(1)I.A. = isopropenyl acetate
(2)CMB = 1-chloro-3-methyl-2-butene
(3)MH = Methylheptenone

EXAMPLE 16

50 g of isopropenyl acetate (0.5 mole), 12.5 g (0.05 mole) of 1-chloro-3,7,11-trimethyl-2,6,10,dodecatriene (farnesyl chloride) and 0.23 g of stannous acetate ($10^{-3}$ g ion $Sn^{2+}$) are introduced into the apparatus used in Example 1.

The procedure of Example 1 is repeated. At the end of the reaction, 5.2 g of farnesyl chloride (degree of conversion 56%) and 1.82 g of farnesylacetone (yield/converted chloride: 25%) are recovered.

EXAMPLE 17

In order to illustrate the catalytic activity of various metal compounds, the following procedure is carried out:

A mixture of 1 part by weight of 1-chloro-3-methyl-2-butene, 4 parts of isopropenyl acetate and $5 \times 10^{-5}$ gram atom of metal per mole of 1-chloro-3-methyl-2-butene are heated to the reflux temperature (95°C), and the amount of methylheptenone in the medium is determined at regular intervals by chromatography. An experiment is carried out under these conditions, by way of control, with the stannous acetate used in Example 1. The results are shown in Table 2.

Table 2

| CATALYSTS | % by weight of methylheptenone after | | | | |
|---|---|---|---|---|---|
| | 10 min | 20 min | 30 min | 1 hr | 2 hr |
| Stannous acetate | 7.8 | | | | |
| Molybdenum (II) acetate | 2.8 | | 5.5 | | |
| AuCl | 2 | | 2.5 | | |
| CoCl$_2$ | | | 1.4 | 2.5 | 4.5 |
| Pb(OOC—CH$_3$)$_2$.3H$_2$O | | | 1 | | 2 |
| CuCl$_2$ | | | | | 1.8 |
| Cd(OOC—CH$_3$)$_2$.2H$_2$O | | | 1.5 | | 2.6 |
| OsCl$_3$ | | | | | 1 |
| UCl$_3$ | 4.7 | 5.2 | | | |
| Co$^{++}$ stearate | 1 | 2.2 | 2.8 | 3.2 | |
| SbCl$_5$ | 3.2 | 3.4 | | | |
| Sn | 4 | 7 | | | |
| Fe(CO)$_5$ | 6.1 | | | | |

I claim:
1. Process for the preparation of a ketone of the formula:

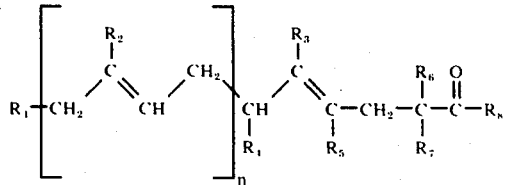

in which:
R$_1$ represents a hydrogen atom or a hydrocarbon group containing up to 10 carbon atoms each of R$_2$ and R$_3$, independently represents a hydrogen atom or an alkyl group of 1 to 4 carbon atoms;

R$_4$ and R$_5$ represent hydrogen atoms or, together they form a divalent hydrocarbon group of the formula $$-CH_2-CH_2-C(CH_3)_2-$$

each of R$_6$ and R$_7$, independently represents a hydrogen atom or a hydrocarbon group containing up to 10 carbon atoms, or R$_6$ and R$_7$ together with the carbon atom, to which they are attached, form a hydrocarbon ring of up to 10 carbon atoms, or the group

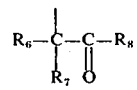

forms a hydrocarbon ring of up to 10 carbon atoms joined through R$_6$ and R$_8$, or R$_7$ and R$_8$, R$_8$ represents a hydrocarbon group containing up to 10 carbon atoms, and n is 0 or an integer of 1 to 6, wherein an unsaturated halide of the general formula:

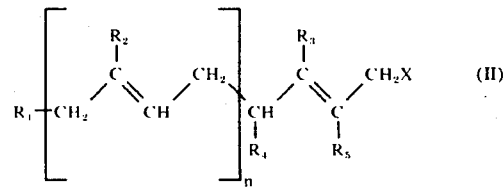

in which X represents a bromine, chlorine or iodine atom and each of R$_1$, R$_2$, R$_3$, R$_4$ and R$_5$ is as defined above, is reacted at a reaction inducing temperature of −50° to +200°C with an ester of the enol form of a ketone, the ester being of the formula:

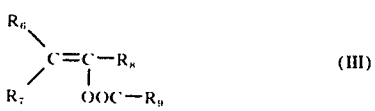

in which each of R$_6$, R$_7$ and R$_8$ is as defined above and R$_9$ represents a hydrocarbon group containing up to 20 carbon atoms, the hydrocarbon group being an alkyl, cycloalkyl or aryl group in the presence of a catalytically effective amount of a catalyst containing a metal from group 1b, 2b, 3b, including the actinide group, 4a, 4b, 5a, 6b, 7b or 8 of the Periodic classification.

2. Process according to claim 1 wherein the reaction is carried out in the presence of an inert organic solvent.

3. Process according to claim 1 wherein said catalyst provides an amount of metal of between $1 \times 10^{-5}$ and $2 \times 10^{-1}$ gram atom of metal or gram ion of metal ion per mole of unsaturated halide.

4. Process according to claim 1 wherein said metal is one of Zr, Mo, W, Mn, Fe, Ru, Au, Os, Cu, Ni, Zn, Cd, Sn, Pb, Sb, Re, U and Co.

5. Process according to claim 1 wherein said ester is present in an excess of at least 0.5 mole per mole of said unsaturated halide.

6. Process according to claim 1 wherein $R_1$ is selected from hydrogen and alkyl, alkenyl, alkadienyl, cycloalkyl, cycloalkenyl and aryl of up to 10 carbon atoms.

7. Process according to claim 6 wherein said unsaturated halide is selected from 1-chloro-3-methyl-2-butane, geranyl chloride and farnesyl chloride.

8. Process according to claim 1 wherein each of $R_6$ and $R_7$ is selected from hydrogen and alkyl, cycloalkyl and aryl of up to 10 carbon atoms.

9. Process according to claim 1 wherein $R_8$ is selected from alkyl, cycloalkyl, aryl, aralkyl and alkaryl of up to 10 carbon atoms.

10. Process according to claim 9 wherein $R^6$ and $R^7$ each represent hydrogen and $R^8$ represents methyl.

11. Process according to claim 1 wherein the catalyst contains a metal of group 4b of the Periodic Classification.

12. Process according to claim 11 wherein the catalyst contains tin.

13. Process according to claim 12 wherein a 1-halogeno-3-methyl-2-butene is reacted with an ester of formula III in which $R^6$ and $R^7$ each represent hydrogen and $R^8$ represents methyl to give 2-methyl-hept-2-en-6-one.

14. Process for the preparation of 2-methylhept-2-en-6-one wherein a 1-bromo, chloro or iodo-3-methyl-2-butene is reacted with an ester of the formula:

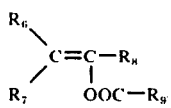

in which $R^6$ and $R^7$ each represent hydrogen and $R^8$ represents methyl at a temperature of $-20°$ C. to $+150°$ C. in the presence of a catalyst containing a metal selected from the group consisting of Zr, Mo, W, Mn, Fe, Ru, Au, Os, Cu, Ni, Zn, Cd, Sn, Pb, Sb, Re, U and Co.

* * * * *